(12) United States Patent
Hu et al.

(10) Patent No.: US 12,310,763 B2
(45) Date of Patent: May 27, 2025

(54) HORIZONTAL PROTECTIVE DEVICE FOR MEDICAL DISPLAY HANGER

(71) Applicant: Maquet (Suzhou) Co. Ltd., Suzhou (CN)

(72) Inventors: Qing Hu, Suzhou (CN); Jin Xuan, Suzhou (CN); Qunhua Li, Suzhou (CN)

(73) Assignee: Maquet (Suzhou) Co. Ltd., Suzhou (CN)

( * ) Notice: Subject to any disclaimer, the term of this patent is extended or adjusted under 35 U.S.C. 154(b) by 470 days.

(21) Appl. No.: 17/787,153

(22) PCT Filed: Jun. 18, 2020

(86) PCT No.: PCT/CN2020/096748
§ 371 (c)(1),
(2) Date: Jun. 17, 2022

(87) PCT Pub. No.: WO2021/120557
PCT Pub. Date: Jun. 24, 2021

(65) Prior Publication Data
US 2023/0016566 A1 Jan. 19, 2023

(30) Foreign Application Priority Data
Dec. 20, 2019 (CN) .......... 201911324026.0

(51) Int. Cl.
*A61B 50/28* (2016.01)
*F16M 11/12* (2006.01)
*F16M 13/02* (2006.01)

(52) U.S. Cl.
CPC .......... *A61B 50/28* (2016.02); *F16M 11/125* (2013.01); *F16M 13/027* (2013.01)

(58) Field of Classification Search
CPC ........ A61B 50/28; A61B 50/20; F16M 11/12; F16M 11/125; F16M 13/027; F16M 11/02; F16M 11/04
(Continued)

(56) References Cited

U.S. PATENT DOCUMENTS

| 4,710,819 A | 12/1987 | Brown | |
| 6,364,268 B1 * | 4/2002 | Metelski | F16M 11/2092 359/368 |

(Continued)

FOREIGN PATENT DOCUMENTS

| CN | 201173371 Y | 12/2008 |
| CN | 104390110 A | 3/2015 |

(Continued)

OTHER PUBLICATIONS

Japan Patent Office, Notice of Reasons for Refusal and Search Report, Application No. 2022-537767, Jun. 19, 2023, 25 pages.

(Continued)

*Primary Examiner* — Eret C McNichols
*Assistant Examiner* — Michael McDuffie
(74) *Attorney, Agent, or Firm* — Quarles & Brady LLP

(57) ABSTRACT

A horizontal protective device for a medical display hanger comprises an upper ring, a middle ring, a lower ring, an upper rotating shaft and a lower rotating shaft. The medical display hanger can be subjected to tilt avoidance in the event of an accidental collision in any horizontal direction.

9 Claims, 2 Drawing Sheets

(58) Field of Classification Search
USPC .......... 248/317, 218.4, 323, 320, 342, 207, 248/220.21, 220.22, 221.11, 298.1
See application file for complete search history.

(56) References Cited

U.S. PATENT DOCUMENTS

| | | | | |
|---|---|---|---|---|
| 7,440,027 | B2* | 10/2008 | Weaver | F16M 13/027 348/375 |
| 7,497,412 | B2* | 3/2009 | Dittmer | F16M 13/02 248/514 |
| 7,575,389 | B2* | 8/2009 | Nance | E05B 47/0045 403/DIG. 1 |
| 8,006,453 | B2* | 8/2011 | Anderson | G09F 7/18 52/39 |
| 10,398,528 | B2* | 9/2019 | Tao | F16C 19/16 |
| 2010/0314513 | A1* | 12/2010 | Evans | F16M 13/027 248/217.4 |
| 2017/0254473 | A1 | 9/2017 | Katz | |

FOREIGN PATENT DOCUMENTS

| | | |
|---|---|---|
| CN | 106233092 A | 12/2016 |
| CN | 205877623 U | 1/2017 |
| CN | 108150778 A | 6/2018 |
| CN | 110836312 A | 2/2020 |
| JP | S60500551 A | 4/1985 |
| JP | 2005221653 A | 8/2005 |
| JP | 2006177879 A | 7/2006 |
| JP | 2006208834 A | 8/2006 |

OTHER PUBLICATIONS

PCT International Search Report and Written Opinion and translation thereof, PCT/CN2020/096748, Sep. 24, 2020, 15 pages.
European Patent Office, Extended European Search Report, Application No. 20902085.8, Jan. 4, 2024, 5 pages.

* cited by examiner

HORIZONTAL PROTECTIVE DEVICE FOR MEDICAL DISPLAY HANGER

CROSS-REFERENCE TO RELATED APPLICATIONS

This application represents the U.S. national stage entry of International Application No. PCT/CN2020/096748 filed Jun. 18, 2020, which claims priority to Chinese Application No. 201911324026.0 filed Dec. 20, 2019, the disclosure of which is incorporated herein by reference in its entirety and for all purposes.

TECHNICAL FIELD

The present invention relates to the technical field of medical instruments, and in particular to a horizontal protective device for a medical display hanger.

BACKGROUND ART

Currently, in hybrid operating rooms, medical equipment and medical staff concentrate around the operating table, and surgical displays (i.e., medical displays) often need to be moved and lifted before or during the operation. In order to protect the patient, the surrounding pendant arm and the medical display itself, it is necessary to avoid accidents and damage caused by rigid collisions when the medical display hanger collides with surrounding people and/or objects accidentally.

SUMMARY OF THE INVENTION

An object of the present invention is to provide a horizontal protective device for a medical display hanger, which can solve the problems existing in the prior art, so that the medical display hanger can be subjected to tilt avoidance in the event of an accidental collision in any horizontal direction.

The above object of the present invention is achieved by a horizontal protective device for a medical display hanger, the horizontal protective device for the medical display hanger comprising an upper ring, a middle ring, a lower ring, an upper rotating shaft and a lower rotating shaft, wherein the upper ring is connected to the bottom of a medical pendant, the lower ring is connected to the top of the medical display hanger, and the middle ring is provided with a total of four holes in front, rear, left, and right portions of the middle ring; one end of the upper rotating shaft is fixedly connected to the upper ring, and the other end of the upper rotating shaft passes through one of the holes of the middle ring to form a shaft-hole clearance fit; one end of the lower rotating shaft is fixedly connected to the lower ring, and the other end of the lower rotating shaft passes through a further one of the holes of the middle ring to form a shaft-hole clearance fit; and the upper rotating shaft and the lower rotating shaft are spatially perpendicular to each other.

According to the above technical solution, the horizontal protective device for the medical display hanger of the present invention can achieve the following beneficial technical effect: the medical display hanger can be subjected to tilt avoidance in the event of an accidental collision in any horizontal direction.

Specifically, the present invention adopts the horizontal protective device for the medical display hanger, the medical display hanger can be subjected to tilt avoidance in the event of an accidental collision in any horizontal direction (e.g., in a left-right direction, front-rear direction, etc., that is, generally in any direction in the horizontal plane), so that the collision is non-rigid. After the collision is released, a medical display can automatically return to its normal state.

Preferably, there are two upper rotating shafts and also two lower rotating shafts, an arrangement direction of the two upper rotating shafts is one of a left-right direction and a front-rear direction, and an arrangement direction of the two lower rotating shafts is the other of the left-right direction and the front-rear direction.

According to the above technical solution, the horizontal protective device for the medical display hanger of the present invention can achieve the following beneficial technical effect: the medical display hanger can be more stable and balanced during the tilt avoidance.

Preferably, the two upper rotating shafts are arranged on the same axis, and the two lower rotating shafts are also arranged on the same axis.

According to the above technical solution, the horizontal protective device for the medical display hanger of the present invention can achieve the following beneficial technical effect: the medical display hanger can be further more stable and balanced during the tilt avoidance.

Preferably, the upper rotating shaft and the lower rotating shaft have the same rotating shaft outer diameter, which is 9.95±0.05 mm.

According to the above technical solution, the horizontal protective device for the medical display hanger of the present invention can achieve the following beneficial technical effect: with a proper rotating shaft outer diameter, the rotation of the rotating shaft relative to the ring can be made smoother and more stable.

Preferably, the four holes have the same hole inner diameter, which is 10.15±0.05 mm.

According to the above technical solution, the horizontal protective device for the medical display hanger of the present invention can achieve the following beneficial technical effect: with a proper hole inner diameter, the rotation of the rotating shaft relative to the ring can be made smoother and more stable.

Preferably, the upper rotating shaft and the lower rotating shaft are located in horizontal planes at different heights.

According to the above technical solution, the horizontal protective device for the medical display hanger of the present invention can achieve the following beneficial technical effect: the upper rotating shaft and the lower rotating shaft can be effectively separated to avoid interference therebetween.

Preferably, the upper rotating shaft is arranged to be higher than the lower rotating shaft by at least 10 mm.

According to the above technical solution, the horizontal protective device for the medical display hanger of the present invention can achieve the following beneficial technical effect: the upper rotating shaft and the lower rotating shaft can be further effectively separated to avoid interference therebetween.

Preferably, the upper rotating shaft and the lower rotating shaft are both stepped rotating shafts, the end of the upper rotating shaft that is fixedly connected to the upper ring is thicker than the other end of the upper rotating shaft that is in clearance fit with the hole, and the end of the lower rotating shaft that is fixedly connected to the lower ring is thicker than the other end of the lower rotating shaft that is in clearance fit with the hole.

According to the above technical solution, the horizontal protective device for the medical display hanger of the present invention can achieve the following beneficial technical effect: the fixation and rotation requirements for the rotating shaft can be better met.

Preferably, the shaft-hole clearance is 0.1-0.3 mm.

According to the above technical solution, the horizontal protective device for the medical display hanger of the present invention can achieve the following beneficial technical effect: with a proper shaft-hole clearance, the rotation of the rotating shaft relative to the ring can be made smoother and more stable.

Preferably, a maximum rotation angle of the upper ring relative to the lower ring is ±5 degrees.

According to the above technical solution, the horizontal protective device for the medical display hanger of the present invention can achieve the following beneficial technical effect: the tilt avoidance range of the medical display hanger can be made more suitable.

LIST OF REFERENCE SIGNS

Figure 1:
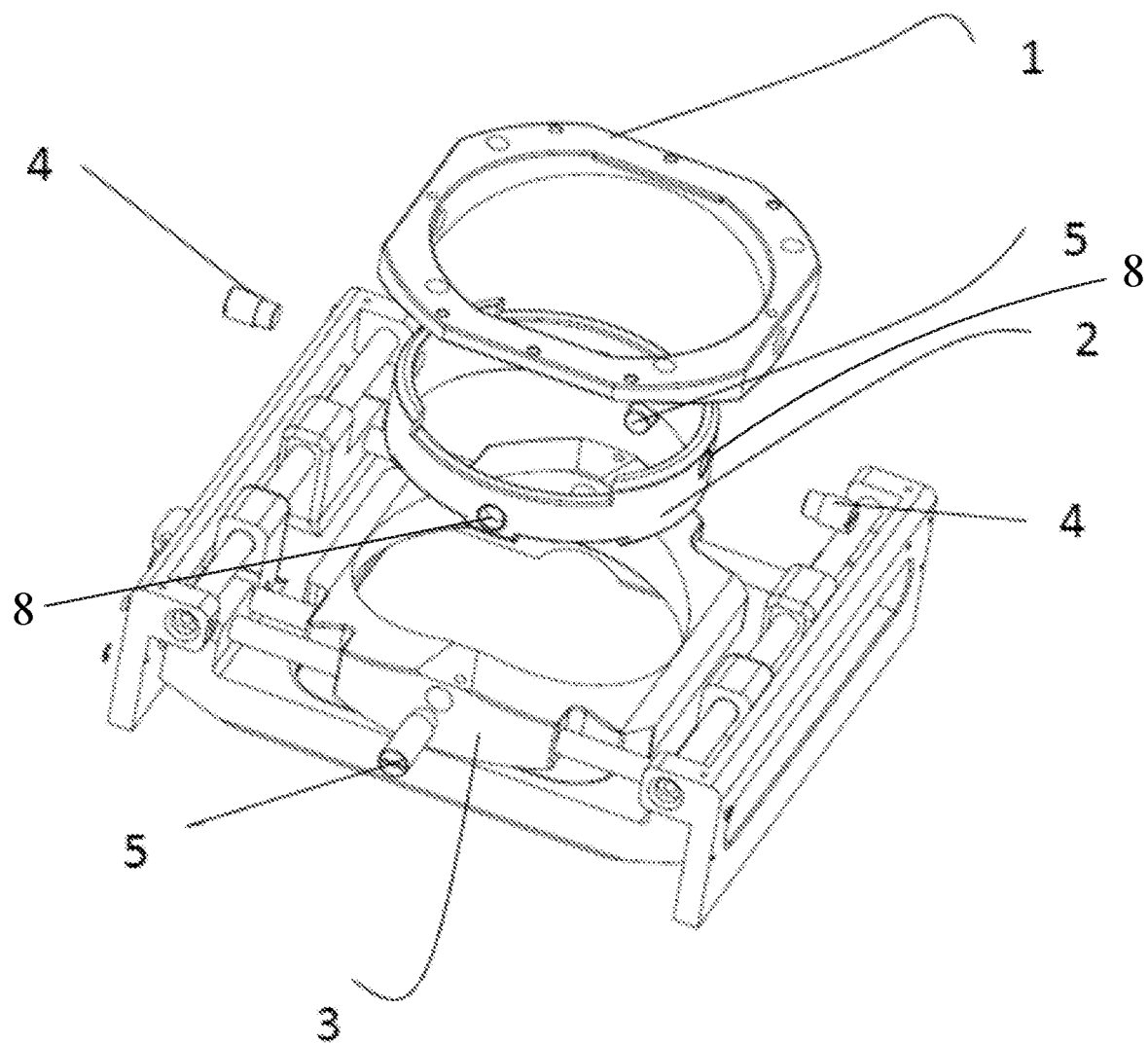
FIG. 1 is a schematic perspective view of a horizontal protective device for a medical display hanger according to an embodiment of the present invention.

1. Upper ring
2. Middle ring
3. Lower ring
4. Upper rotating shaft
5. Lower rotating shaft
6. Medical pendant
7. Medical display hanger
8. Hole
10. Horizontal protective device for medical display hanger

DETAILED DESCRIPTION OF EMBODIMENT

The specific embodiments of the present invention will be described below. It should be pointed out that in the detailed description of these embodiments, it is not possible for this description to describe in detail all the features of the actual embodiments for the sake of brevity and simplicity of description. It should be understood that in the actual implementation of any one embodiment, as in the course of any engineering project or design project, in order to achieve the developer's specific objectives and meet system-related or business-related constraints, a variety of specific decisions are often made, and thus any change may occur from one embodiment to another. Moreover, it is also understandable that although the efforts made during such development may be complex and lengthy, for those of ordinary skill in the art related to the disclosure of the present invention, some changes in design, manufacturing or production based on the technical content disclosed in the present disclosure are only conventional technical means, and it should not be understood that the content of the present disclosure is insufficient.

Unless otherwise defined, the technical terms or scientific terms as used in the claims and the description should be construed in a generic meaning as understood by those of ordinary skill in the art to which the present invention pertains. The terms "first", "second" or the like as used in the description and claims of the patent application of the present invention do not denote any order, quantity, or importance, but are merely used to distinguish different components. The terms "a", "an" or the like do not denote a quantity limitation, but mean that there is at least one. The terms "include", "comprise" or the like mean that the elements or objects that precede "include" or "comprise" encompass the elements or objects and their equivalents that appear after "include" or "comprise" and do not exclude other elements or objects. The terms "connect", "connected" or the like are not limited to physical or mechanical connections, nor are they limited to direct or indirect connections.

It should be noted that the terms "upper", "lower", "front", "rear", "left", "right", etc. used herein are exemplary directions defined only for facilitating the description of the present invention. As shown in FIG. 1, the direction toward the reader is "front", and the direction away from the reader is "rear", the direction of the bottom side in the paper is "lower", the direction of the top side in the paper is "upper", the direction of the left side in the paper is "left", and the direction of the right side in the paper is "right". In order to show the details better, a front surface (front face) of a horizontal protective device for a medical display hanger in FIG. 1 is slightly inclined with respect to the layout direction of the paper. Of course, on the basis of the present invention, those skilled in the art would be able to understand that the directions such as "upper", "lower", "front", "rear", "left", and "right" can be defined in other ways, which also fall within the scope of protection of the present invention.

Figure 2:
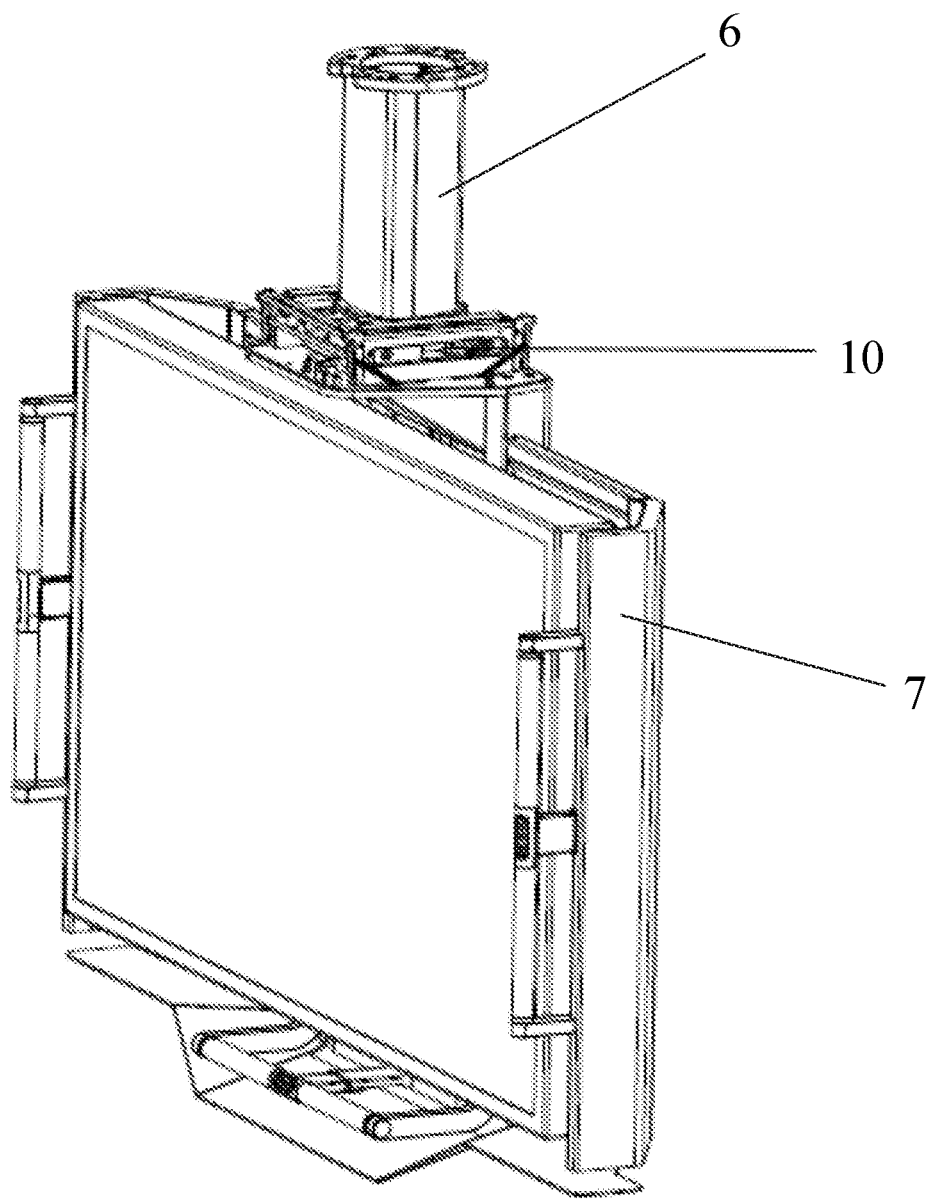
FIG. 2 is a schematic installation diagram of a horizontal protective device for a medical display hanger according to an embodiment of the present invention.

FIG. 1 is a schematic perspective view of a horizontal protective device for a medical display hanger according to an embodiment of the present invention. FIG. 2 is a schematic installation diagram of a horizontal protective device for a medical display hanger according to an embodiment of the present invention.

As shown in FIGS. 1 and 2, according to an embodiment of the present invention, a horizontal protective device 10 for a medical display hanger includes an upper ring 1, a middle ring 2, a lower ring 3, an upper rotating shaft 4 and a lower rotating shaft 5. The upper ring 1 is connected to the bottom of a medical pendant 6, the lower ring 3 is connected to the top of the medical display hanger 7, and the middle ring 2 is provided with a total of four holes 8 in front, rear, left, and right portions thereof. One end of the upper rotating shaft 4 is fixedly connected to the upper ring 1, and the other end of the upper rotating shaft 4 passes through one of the holes 8 of the middle ring 2 to form a shaft-hole clearance fit. One end of the lower rotating shaft 5 is fixedly connected to the lower ring 3, and the other end of the lower rotating shaft 5 passes through a further one of the holes 8 of the middle ring 2 to form a shaft-hole clearance fit. The upper rotating shaft 4 and the lower rotating shaft 5 are spatially perpendicular to each other.

According to the above technical solution, the horizontal protective device for the medical display hanger of the present invention can achieve the following beneficial technical effect: the medical display hanger can be subjected to tilt avoidance in the event of an accidental collision in any horizontal direction.

Specifically, the present invention adopts the horizontal protective device for the medical display hanger, the medical display hanger can be subjected to tilt avoidance in the event of an accidental collision in any horizontal direction (e.g., in a left-right direction, front-rear direction, etc., that is, generally in any direction in the horizontal plane), so that the collision is non-rigid. After the collision is released, a medical display can automatically return to its normal state.

That is to say, one end of the upper rotating shaft 4 is fixedly connected (e.g., threadedly connected) to the upper ring 1, and the other end of the upper rotating shaft 4 passes through one of the holes 8 of the middle ring 2 to form a shaft-hole clearance fit, thus the middle ring 2 can rotate relative to the upper ring 1, with a rotating axis being the upper rotating shaft 4.

One end of the lower rotating shaft 5 is fixedly connected (e.g., threadedly connected) to the lower ring 3, and the other end of the lower rotating shaft 5 passes through a further one of the holes 8 of the middle ring 2 to form a shaft-hole clearance fit, thus the middle ring 2 can rotate relative to the lower ring 3, with a rotating axis being the lower rotating shaft 5.

Therefore, the medical display hanger can not only rotate about the upper rotating shaft 4, but also rotate about the lower rotating shaft 5, and can further rotate about the upper rotating shaft 4 and the lower rotating shaft 5 at the same time, thereby realizing tilt avoidance in any horizontal direction.

It should be noted that the upper ring 1, the middle ring 2, and the lower ring 3 are all ring-shaped structures. The term "ring" here is not limited to a circular ring, and a substantially square ring, a polygonal ring, etc. may also be used, as long as there is enough space inside the "ring" for a cable to pass through. Therefore, the cable can pass through the horizontal protective device for the medical display hanger, without causing possible clamping and damage to the cable during movement, and the cable routing of the present invention is more compact and simplified.

Preferably, the upper ring 1 is connected to the bottom of the medical pendant 6, for example, to a cylindrical structure at the bottom of the medical pendant 6, as shown in FIG. 2.

Preferably, as shown in FIG. 1, the middle ring 2 is provided with a total of four holes 8 in the front, rear, left, and right portions thereof. That is to say, the middle ring 2 is provided with one hole 8 respectively on its front side, rear side, left side and right side, for a total of four holes 8. Preferably, adjacent holes 8 are spaced apart by 90 degrees from each other on the periphery of the middle ring 2.

Preferably, the middle ring 2 has a smaller diameter relative to the upper ring 1 and the lower ring 3, so that the upper rotating shaft 4 may pass through one of the holes 8 of the middle ring 2 from the outside of the middle ring 2, and the lower rotating shaft 5 may pass through a further one of the holes 8 of the middle ring 2 from the outside of the middle ring 2.

Preferably, the hole 8 may be a through hole, to facilitate the processing and formation of the hole.

Preferably, as shown in FIG. 1, there are two upper rotating shafts 4 and also two lower rotating shafts 5, an arrangement direction of the two upper rotating shafts 4 is one of a left-right direction and a front-rear direction, and an arrangement direction of the two lower rotating shafts 5 is the other of the left-right direction and the front-rear direction. For example, the arrangement direction of the two upper rotating shafts 4 is the left-right direction, and the arrangement direction of the two lower rotating shafts 5 is the front-rear direction.

According to the above technical solution, the horizontal protective device for the medical display hanger of the present invention can achieve the following beneficial technical effect: the medical display hanger can be more stable and balanced during the tilt avoidance.

Of course, the two upper rotating shafts and the two lower rotating shafts are only a preferred form utilized by the horizontal protective device for the medical display hanger of the present application, those skilled in the art can understand on the basis of the disclosure of the present application that other suitable numbers of rotating shafts, such as one upper rotating shaft and one lower rotating shaft, may also be used without departing from the scope of protection of the claims of the present application. Compared to the technical solution with one upper rotating shaft and one lower rotating shaft, the technical solution with two upper rotating shafts and two lower rotating shafts can make the medical display hanger more stable and balanced during the tilt avoidance.

Preferably, as shown in FIG. 1, the two upper rotating shafts 4 are arranged on the same axis, and the two lower rotating shafts 5 are also arranged on the same axis. For example, the two upper rotating shafts 4 are arranged on the same axis in the left-right direction, and the two lower rotating shafts 5 are arranged on the same axis in the front-rear direction. Preferably, the axis on which the two upper rotating shafts 4 are located and the axis on which the two lower rotating shafts 5 are spatially perpendicular to each other.

According to the above technical solution, the horizontal protective device for the medical display hanger of the present invention can achieve the following beneficial technical effect: the medical display hanger can be further more stable and balanced during the tilt avoidance.

Preferably, the upper rotating shaft 4 and the lower rotating shaft 5 have the same rotating shaft outer diameter, which is 9.95±0.05 mm.

According to the above technical solution, the horizontal protective device for the medical display hanger of the present invention can achieve the following beneficial technical effect: with a proper rotating shaft outer diameter, the rotation of the rotating shaft relative to the ring can be made smoother and more stable.

Preferably, the four holes 8 have the same hole inner diameter, which is 10.15±0.05 mm.

According to the above technical solution, the horizontal protective device for the medical display hanger of the present invention can achieve the following beneficial technical effect: with a proper hole inner diameter, the rotation of the rotating shaft relative to the ring can be made smoother and more stable.

Preferably, as shown in FIG. 1, the upper rotating shaft 4 and the lower rotating shaft 5 are located in horizontal planes at different heights. That is to say, the axis on which the upper rotating shaft 4 is located and the axis on which the lower rotating shaft 5 is located are spatially perpendicular to each other, but are offset from each other in height.

According to the above technical solution, the horizontal protective device for the medical display hanger of the present invention can achieve the following beneficial technical effect: the upper rotating shaft and the lower rotating shaft can be effectively separated to avoid interference therebetween.

Preferably, the upper rotating shaft 4 is arranged to be higher than the lower rotating shaft 5 by at least 10 mm.

According to the above technical solution, the horizontal protective device for the medical display hanger of the present invention can achieve the following beneficial technical effect: the upper rotating shaft and the lower rotating shaft can be further effectively separated to avoid interference therebetween.

Preferably, as shown in FIG. 1, the upper rotating shaft 4 and the lower rotating shaft 5 are both stepped rotating shafts, the end of the upper rotating shaft 4 that is fixedly connected to the upper ring is thicker than the other end of the upper rotating shaft 4 that is in clearance fit with the hole, and the end of the lower rotating shaft 5 that is fixedly connected to the lower ring is thicker than the other end of the lower rotating shaft 5 that is in clearance fit with the hole.

According to the above technical solution, the horizontal protective device for the medical display hanger of the present invention can achieve the following beneficial technical effect: the fixation and rotation requirements for the rotating shaft can be better met.

That is to say, the end of the rotating shaft that is fixedly connected to the ring is thicker, which can allow for more stable fixation between the rotating shaft and the ring; and the other end of the rotating shaft that is in clearance fit with the hole is thinner, which can appropriately reduce the height of the middle ring, so that the size of the entire horizontal protective device is appropriately reduced.

Preferably, the shaft-hole clearance is 0.1-0.3 mm.

According to the above technical solution, the horizontal protective device for the medical display hanger of the present invention can achieve the following beneficial technical effect: with a proper shaft-hole clearance, the rotation of the rotating shaft relative to the ring can be made smoother and more stable.

Preferably, a maximum rotation angle of the upper ring 1 relative to the lower ring 3 is ±5 degrees.

That is to say, as shown in FIG. 1, in an original state of the horizontal protective device for the medical display hanger, the upper ring 1 and the lower ring 3 are both located in horizontal planes. If the front, lower part (relative to the horizontal protective device) of the medical display hanger is hit in the horizontal direction, when viewed from the front, the lower ring 3 will rotate downwardly about the upper rotating shaft 4 relative to the upper ring 1, and the maximum rotation angle is 5 degrees downward. If the rear, lower part (relative to the horizontal protective device) of the medical display hanger is hit in the horizontal direction, when viewed from the front, the lower ring 3 will rotate upwardly about the upper rotating shaft 4 relative to the upper ring 1, and the maximum rotation angle is 5 degrees upward. Likewise, if the medical display hanger is hit in other horizontal directions, the protective principle and the rotation range of the horizontal protective device are similar to the above. Therefore, the maximum rotation angle of the upper ring 1 relative to the lower ring 3 is ±5 degrees.

According to the above technical solution, the horizontal protective device for the medical display hanger of the present invention can achieve the following beneficial technical effect: the tilt avoidance range of the medical display hanger can be made more suitable.

Of course, the maximum rotation angle of ±5 degrees is only a preferred form utilized by the horizontal protective device for the medical display hanger of the present application, those skilled in the art can understand on the basis of the disclosure of the present application that other suitable maximum rotation angles may also be used, such as ±3 degrees, ±4 degrees, ±6 degrees, ±7 degrees, ±8 degrees, ±9 degrees, ±10 degrees, etc., without departing from the scope of protection of the claims of the present application. Compared to the technical solutions with other maximum rotation angles, the technical solution with the maximum rotation angle of ±5 degrees can make the tilt avoidance range of the medical display hanger more suitable, which enables effective tilt avoidance, but also avoid losing stability due to large tilt avoidance.

Preferably, the limit to rotation is realized by the movement interference of the upper ring 1, the middle ring 2 and the lower ring 3 themselves at extreme positions.

The specific implementations of the present invention are described above. However, it would be understood by those skilled in the art that the above specific implementations do not constitute the limitations on the present invention, and those skilled in the art may make various modifications on the basis of the above disclosure without departing from the scope of the present invention.

The invention claimed is:

1. A horizontal protective device for a medical display hanger, wherein the horizontal protective device for the medical display hanger comprises an upper ring, a middle ring, a lower ring, an upper rotating shaft and a lower rotating shaft, wherein the upper ring is connected to the bottom of a medical pendant, the lower ring is connected to the top of the medical display hanger, and the middle ring is provided with a total of four holes in front, rear, left, and right portions of the middle ring; one end of the upper rotating shaft is fixedly connected to the upper ring, and the other end of the upper rotating shaft passes through one of the holes of the middle ring to form a shaft-hole clearance fit; one end of the lower rotating shaft is fixedly connected to the lower ring, and the other end of the lower rotating shaft passes through a further one of the holes of the middle ring to form a shaft-hole clearance fit; and the upper rotating shaft and the lower rotating shaft are spatially perpendicular to each other;

wherein there are two upper rotating shafts and also two lower rotating shafts, an arrangement direction of the two upper rotating shafts is one of a left-right direction and a front-rear direction, and an arrangement direction of the two lower rotating shafts is the other of the left-right direction and the front-rear direction.

2. The horizontal protective device for a medical display hanger of claim 1, wherein the two upper rotating shafts are arranged on the same axis, and the two lower rotating shafts are also arranged on the same axis.

3. The horizontal protective device for a medical display hanger of claim 1, wherein the upper rotating shaft and the lower rotating shaft have the same rotating shaft outer diameter, which is 9.95±0.05 mm.

4. The horizontal protective device for a medical display hanger of claim 1, wherein the four holes have the same hole inner diameter, which is 10.15±0.05 mm.

5. The horizontal protective device for a medical display hanger of claim 1, wherein the upper rotating shaft and the lower rotating shaft are located in horizontal planes at different heights.

6. The horizontal protective device for a medical display hanger of claim 5, wherein the upper rotating shaft is arranged to be higher than the lower rotating shaft by at least 10 mm.

7. The horizontal protective device for a medical display hanger of claim 1, wherein the upper rotating shaft and the lower rotating shaft are both stepped rotating shafts, the end of the upper rotating shaft that is fixedly connected to the upper ring is thicker than the other end of the upper rotating shaft that is in clearance fit with the hole, and the end of the lower rotating shaft that is fixedly connected to the lower ring is thicker than the other end of the lower rotating shaft that is in clearance fit with the hole.

8. The horizontal protective device for a medical display hanger of claim 1, wherein the shaft-hole clearance is 0.1-0.3 mm.

9. The horizontal protective device for a medical display hanger of claim 1, wherein a maximum rotation angle of the upper ring relative to the lower ring is ±5 degrees.

* * * * *